Figure 1:
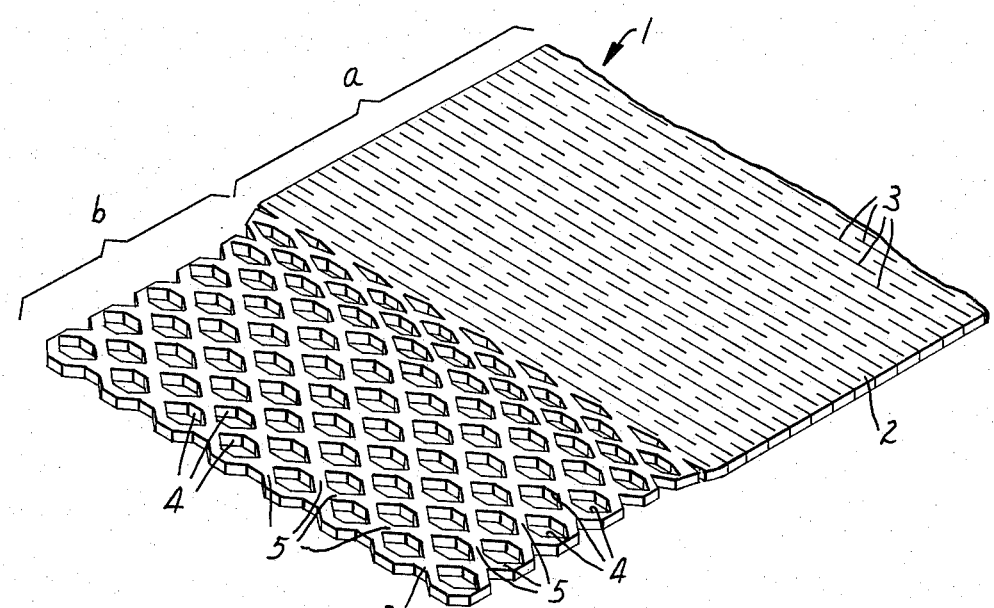

United States Patent [19]

Thill

[11] 4,294,240
[45] Oct. 13, 1981

[54] PERFORATED CLOSED CELL PADDING MATERIAL

[75] Inventor: Gary A. Thill, Saint Paul, Minn.

[73] Assignee: Minnesota Mining and Manufacturing Company, Saint Paul, Minn.

[21] Appl. No.: 67,394

[22] Filed: Aug. 17, 1979

Related U.S. Application Data

[63] Continuation of Ser. No. 815,857, Jul. 14, 1977, abandoned.

[51] Int. Cl.³ ............................................. A61L 15/00
[52] U.S. Cl. ...................................... 128/156; 128/83
[58] Field of Search ................. 128/155, 156, 157, 90, 128/89, 83, 82; 428/136, 310, 158

[56] References Cited

U.S. PATENT DOCUMENTS

| | | | |
|---|---|---|---|
| 3,476,109 | 11/1969 | Hurney | 128/157 |
| 3,763,858 | 10/1973 | Buese | 128/156 |

FOREIGN PATENT DOCUMENTS

| | | | |
|---|---|---|---|
| 1275541 | 5/1972 | United Kingdom | 128/90 UX |
| 1304939 | 1/1973 | United Kingdom | 128/90 UX |

*Primary Examiner*—John D. Yasko
*Attorney, Agent, or Firm*—Cruzan Alexander; Donald M. Sell; Gary L. Griswold

[57] ABSTRACT

Perforated closed cell foam padding material useful with orthopedic devices, said material being capable of passing perspiration from human skin therethrough, being resiliently compressible, and being elastic in the longitudinal direction of the padding material.

8 Claims, 2 Drawing Figures

PERFORATED CLOSED CELL PADDING MATERIAL

This is a continuation of Application Ser. No. 815,857 filed July 14, 1977 now abandoned.

This invention relates to a perforated, closed cell foam padding material useful with orthopedic devices.

Treatment of body skeletal abnormalities such as bone fractures usually involves the immobilization of a portion of the body. Such immobilization is provided by casts such as those made of plaster of paris or fabric impregnated with plaster of paris. More recently casts have been made of polymeric materials such as those described in U.S. Pat. Nos. 3,882,857; 3,881,473; 3,908,644; 3,809,600; and 3,692,023.

Such casts normally must remain in place on the body for a long period of time and often result in considerable discomfort and trauma to the patient. Such trauma is caused by chafing and pressure against the cast provided by various protuberances of the anatomy. Chafing and pressure results in ulceration of the skin and tissue overlying the protuberance. A further cause of discomfort and trauma is the entrapment of moisture which is continually perspired from human skin under the cast. Entrapment of such moisture causes such problems as itching and skin maceration.

Various attempts have been made to alleviate the aforesaid problems including providing padding materials under casts to provide a cushion between the cast and body and providing porous casts and/or nonwetting porous padding material to allow for moisture vapor transmission. Traditionally cotton fabric or similar hydrophilic material was used as padding material under casts to provide a protection for the skin under the cast. However, such materials absorb moisture and thus provide a place for the moisture to accumulate causing the aforesaid problems with entrapped moisture under casts. Furthermore, such materials become permanently compressed under the cast. As the body becomes smaller through nonuse or atrophies these materials did not expand to decrease the gap between the cast and body. It is necessary that this gap be filled to preserve immobilization of the body under the cast. Other padding materials are described in the aforesaid U.S. patents. These include stockinet material of knitted or woven, nonwetting, crystalline polypropylene material (U.S. Pat. No. 3,881,473), sleeves made of polyethylene or polypropylene yarn (U.S. Pat. No. 3,882,857), and woven or nonwoven relatively water repellent material such as polypropylene or polyester (U.S. Pat. No. 3,908,644). The aforesaid materials have not resulted in a padding material which does not absorb moisture yet allows for moisture vapor transmission and provides a resilient cushion between the cast and body.

Applicant has discovered a padding material which does not absorb moisture yet provides a resilient cushion and allows for water vapor transmission. The padding material is resiliently compressible so that as the portion of the body in the cast becomes smaller through nonuse the compressed padding material expands to assist in filling the enlarged gap between the cast and the body. Applicant's padding material comprises a padding material useful with orthopedic devices consisting essentially of a closed cell polymeric foam, said foam being water repellent at least to the extent that water penetrates the foam with difficulty, said padding material being conformable, being resiliently compressible, containing perforations capable of passing perspiration from human skin therethrough, and being elastic in the longitudinal direction of said padding material.

Applicant's padding material will be described in detail with reference to the drawings in which FIG. 1 is a perspective view of the padding with portions in a relaxed condition and portions in a stretched condition.

Figure 2:
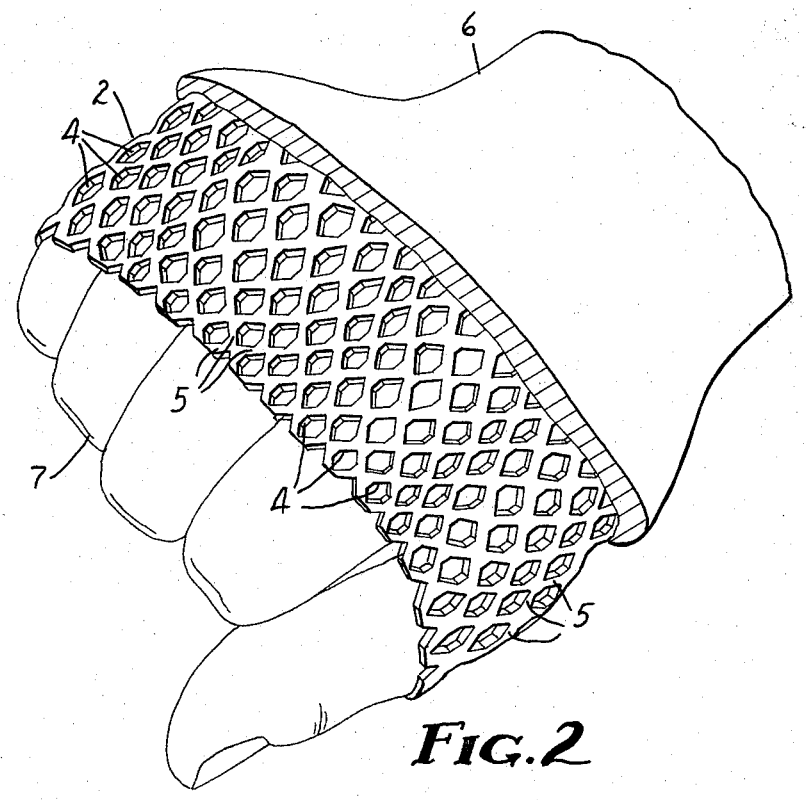

FIG. 2 illustrates the padding material in a stretched condition as applied to a fractured limb, said padding material covering a boney protuberance.

Specifically, in FIG. 1 the padding material 1 comprises closed cell foam 2 containing slits 3 in relaxed portion a of the padding 1. In the stretched portion b of the padding 1 the slits 3 have been expanded to become hexagonal shaped perforations 4. The shape of the perforations 4 depends on the degree of stretching. With more stretching they are diamond shaped. The padding 1 in portion b is stretched to approximately twice its length before stretching. As will be noted from FIG. 1 the slits 3 are in parallel rows with slits 3 from adjacent rows being offset from the slits 3 in the next adjacent row. The rows are parallel and are perpendicular to the longitudinal dimension of the padding 1. Each hexagonal shaped perforation 4 is surrounded by closed cell foam 2 which is, at its narrowest point 5, no less in width than the thickness of the foam. This allows the padding, when applied longitudinally, to lie flat rather than roll at the edges. Such rolling produces an accumulation of the padding under the cast causing ridges which can form pressure points.

The padding 1 shown in FIG. 2 is applied over the knuckles of a hand 7 and contains hexagonal perforations 4. Also shown in FIG. 2 is a section of the cast 6 which has been cut away to expose the padding material 1 thereunder covering the portion of the body containing the protuberances, i.e., knuckles.

The closed cell foam in the padding material of the present invention is water repellent at least to the extent that water penetrates the foam with difficulty. The foam does not absorb moisture to any significant degree. The preferred polymeric materials utilized in making the foam are polyethylene, polypropylene, and similar materials. Closed cell water repellent polyurethane foams and polystyrene foam can also be used. The foam material is closed cell in order that the foam not absorb water or moisture which transpires from the skin or water vapor which somehow finds its way through or under the cast. The most preferred foam is a polyethylene closed cell foam which is approximately 1/16 in. (0.16 cm) thick and has a density of about 4 pounds per cubic foot (0.064 gm/cc). Preferably the foam will be from approximately 1/32 in. (0.08 cm) to about 3/16 in. (0.48 cm) thick.

The padding material is conformable so that when applied to the body it will conform to the shape of the body including conforming to protuberances on the body such as elbows, knees, knuckles, etc. The padding material is resiliently compressible. When applied to the body the padding is wrapped upon itself and is somewhat compressed by such wrapping and by having the cast material applied over it. However, the compression does not cause permanent deformation of the padding. This allows the foam to resiliently expand when the body atrophies as above described and continues to fill the void between the cast and the body to maintain a tight relationship between the cast and the body.

The closed cell foam material is water repellent. However, the padding must be water permeable. This water permeability is obtained by means of perforations. The perforations are placed within and through the foam in such a configuration so as to provide a close proximity between perforations thus allowing moisture to escape through the perforations and not be blocked by the closed cell foam. However, the distance between perforations is normally greater than the thickness of the foam to prevent the above described edge rolling of the foam. Normally in a stretched or expanded condition (twice the unstretched length) perforations in the padding comprise at least about 50% of the area of the padding.

The preferred configuration for the slits 3 which become perforations 4 is shown in FIG. 1. In the relaxed state the perforations are preferably rows of slits, which slits are 0.4 in. (1.0 cm) in length. The rows of slits are approximately 0.065 in. (0.165 cm) apart in the longitudinal direction of the padding and the slits in a row are approximately 0.12 in. (0.3 cm) apart. The slits in adjacent rows are offset from each other.

The preferred foam is manufactured by forming extruded polyethylene film using a blowing agent and applied heat. The closed cell foam is then slit by placing the foam over a roll which provides skipped slits perpendicular to the machine direction of the roll. The slitting is done with the dimensions and specifications as set forth above and as shown in FIG. 1.

The perforations or slits in the foam provide sufficient porosity in the padding to pass perspiration from human skin therethrough. The perforations also allow the foam to be elastic in the longitudinal direction of the padding so that it can be stretched around the body prior to application of the cast. The perforations as described are slits which become hexagons or diamonds. Other geometrical perforations such as circles or polygons may optionally be included in addition to the slits. It is necessary that the perforations be so disposed to allow for elasticity of the padding in a longitudinal direction of the padding. With the preferred slit configuration there is reduced tension in the padding when it is in place and sufficient porosity remains when successive layers overlap.

In use the padding is stretched as it is applied over the body. Normally there is some overlap of the padding on itself with the normal thickness of the padding under a cast being from 1 to 2 thicknesses of the padding. Thicker applications may be made over large protuberances. The padding is somewhat self-adhesive to itself which assists in its application to the body and in overlapping itself. The cast material is applied over the padding material. Moisture which evolves from the skin under the cast is removed by means of the perforations in the padding. There is some movement of the padding under the cast which assists in negating skin maceration by providing porosity at different times directly over the majority of the skin under the padding.

What is claimed is:

1. A combination for rendering a portion of the body relatively immobile, said combination comprising an orthopedic device which renders the portion of the body relatively immobile and a padding material, said padding material consisting essentially of a closed cell polymeric foam, said foam being water repellent at least to the extent that water penetrates the foam with difficulty, said padding material being conformable, being resiliently compressible, containing perforations capable of passing perspiration from human skin therethrough and being elastic in the longitudinal direction.

2. The combination of claim 1 wherein said foam is polyethylene.

3. The combination of claim 1 wherein said perforations are slits.

4. The combination of claim 3 wherein said perforations, when said padding material is in a relaxed state, are slits perpendicular to the longitudinal dimension of said padding material, said slits being in parallel rows across the lateral dimension of said padding material with slits of adjacent rows being offset from each other, said slits perforating through the thickness of said padding material.

5. A method for rendering a portion of the body relatively immobile, said method comprising the steps of:
   a. applying a padding material to the portion of the body which is to be rendered immobile; and
   b. applying over said padding material an orthopedic device which renders the portion of the body relatively immobile;

wherein said padding material consists essentially of a closed cell polymeric foam, said foam being water repellent at least to the extent that water penetrates the foam with difficulty, said padding material being conformable, being resiliently compressible, containing perforations capable of passing perspiration from human skin therethrough, and being elastic in the longitudinal direction.

6. The method of claim 5, wherein said foam is polyethylene.

7. The method of claim 5 wherein said perforations are slits.

8. The method of claim 7 wherein said perforations, when said padding material is in a relaxed state, are slits perpendicular to the longitudinal dimension of said padding material, said slits being in parallel rows across the lateral dimension of said padding material with slits of adjacent rows being offset from each other, said slits perforating through the thickness of said padding material.

* * * * *